United States Patent [19]

Petrille et al.

[11] 3,950,401
[45] Apr. 13, 1976

[54] OLEFIN SULFONATES

[75] Inventors: Dennis G. Petrille, Naperville; Robert E. Karll, Batavia, both of Ill.

[73] Assignee: Standard Oil Company, Chicago, Ill.

[22] Filed: Nov. 18, 1974

[21] Appl. No.: 524,560

Related U.S. Application Data

[63] Continuation of Ser. No. 316,840, Dec. 20, 1972, abandoned.

[52] U.S. Cl. .............................................. 260/504 R
[51] Int. Cl.² ........................................... C07B 13/00
[58] Field of Search ................ 260/504 R, 513 R

[56] References Cited
UNITED STATES PATENTS 2,677,702    5/1954    Bloch et al. ......................... 260/513

3,420,875    1/1969    Di Salvo et al. .................... 260/513

*Primary Examiner*—James O. Thomas, Jr.
*Assistant Examiner*—A. Siegel
*Attorney, Agent, or Firm*—Edwin C. Lehner; Arthur G. Gilkes; William T. McClain

[57] ABSTRACT

Viscous liquid propene or butene polymers having number average molecular weights of about 250–500 are converted to the corresponding oil-soluble ammonium alkenyl sulfonates by treatment of the polymer with gaseous sulfur trioxide in a falling-film reactor, separation of the oil-soluble polymer sulfonic acids and oil-soluble polymer sultones from the sulfonation product mixture, and neutralization of the sulfonic acids and sultones with anhydrous ammonia.

5 Claims, No Drawings

OLEFIN SULFONATES

This is a continuation of application Ser. No. 316,840, filed Dec. 20, 1972, now abandoned.

FIELD OF THE INVENTION

This invention relates to the preparation of oil-soluble ammonium alkenyl sulfonates wherein the alkenyl moiety is a propene or butene polymer having a number average molecular weight in the range of about 250–500.

SUMMARY OF THE INVENTION

It has been discovered that viscous liquid propene or butene polymers having number average molecular weights in the range of about 250–500 and about 80 to 95 mol percent olefinic unsaturation, the balance being paraffins, can be used as feedstocks for preparation of oil-soluble alkenyl sulfonic acids by means of falling-film sulfonation procedures.

The process of the invention for preparing oil-soluble ammonium alkenyl sulfonates wherein the alkenyl moiety is a propene or butene polymer having a number average molecular weight of about 250 to about 500 comprises (a) continuously treating in a falling-film reactor a viscous liquid propene or butene polymer having a number average molecular weight of about 250 to about 500 with about 1.7 to about 2.1 mols of sulfur trioxide per mol of said polymer by cocurrently passing a liquid film of said polymer and a gaseous stream of sulfur trioxide diluted with an inert gas thru said reactor while maintaining an excess of sulfur trioxide in contact with said film during passage of said liquid film thru said reactor to form a crude acid mixture comprising the corresponding alkene sulfonic acids and sultones of said polymer; (b) admixing said acid mixture with about 0.25 to about 1.25 volumes of a water immiscible inert liquid hydrocarbon solvent per volume of acid mixture and about 3 to about 20, preferably 5 to 10, weight percent of water based on said acid mixture, holding with agitation the aqueous mixture at a temperature of about 70° to 175°F for about 0.25 to about 2 hours, thereafter separating the aqueous hydrocarbon solvent phases and recovering the hydrocarbon solvent organic phase containing oil-soluble alkenyl sulfonic acid and polymer sultones; (c) treating at atmospheric pressure the solvent phase of step b with anhydrous ammonia at a temperature of about 100° to about 170°F in an amount sufficient to neutralize said sulfonic acid and provide a basic mixture comprising ammonium alkenyl sulfonate and polymer sultone; and (d) heating at atmospheric pressure the basic mixture of step c in the presence of anhydrous ammonia, in an amount sufficient to maintain said mixture basic, to a temperature of about 290° to about 340°F and holding said basic mixture at said temperature for a period of time sufficient to reduce the sultone content thereof and form additional ammonium alkenyl sulfonates.

The crude acid mixture obtained in the sulfonation step is a complex mixture of mono-, di-, and poly -alkene sulfonic acids, sultones, sulfonated by-products, and unreacted polymer which acts as a carrier or diluent for the sulfonated materials.

It has been found that conventional neutralization of the crude acid mixture with aqueous monovalent bases is unsatisfactory because of the formation of hydroxy alkyl sulfonates from the sultones and a large amount of oil-insoluble materials that are difficult to remove from the neutralized product.

In accordance with the invention, separation of substantially oil-soluble sulfonic acids and oil-soluble sultones from the crude acid mixture is essential prior to neutralization. The two-step neutralization of the purified sulfonic acid and sultone mixture with anhydrous ammonia substantially reduces the sultone content and increases the yield of ammonium alkenyl sulfonates. Infra-red analysis of the neutralized product did not show the presence of hydroxy alkyl sulfonates.

DESCRIPTION OF PREFERRED EMBODIMENT

Liquid polybutene (butene polymer having a number average molecular weight of about 340) was introduced into a slot-type falling-film reactor of the type described in U.S. Pat. No. 3,328,460 at a rate of 388 pounds per hour. The reactor was 22 feet long with a slot dimension of ⅝ inch by 24 inches. The film temperature in the reactor was 80°–122°F. Gaseous sulfur trioxide diluted with air, at a molar rate of 1.93 mols per mol of polybutene, was introduced cocurrently to the film in the reactor at a rate of 170 pounds per hour and air rate of 900 cubic feet per minute at 18 psig. Liquid residence time was about 125 to 150 seconds in the reactor. The crude acid mix from the reactor had a total activity of about 72 weight percent, contained about 46 weight percent sulfonic acid, about 7 weight percent hexane-insoluble sludge, and about 19 weight percent sultone.

The crude acid mix was diluted with an equal volume of hexane and 10 weight percent water. The aqueous mixture was held with agitation at 130°–140°F for 1 hour in a holding-settling tank. After a 2 hour settling period, the aqueous phase was drawn off and the hexane-acid phase transferred to a reactor for neutralization.

Neutralization of the sulfonic acid-sultone mixture in hexane was effected by introducing anhydrous ammonia into the mixture at a rate of two cubic feet per hour per gallon while maintaining temperature of the mixture below 150°F until a color change of from black to amber is noted which indicated neutralization of the sulfonic acid. At that point the ammonia rate was reduced to 0.5 cubic feet per hour per gallon and the temperature of the mixture raised to drive off hexane and water to a temperature of 310°F. The mixture was held at 310°F with continued introduction of ammonia for 2 hours to reduce the sultone content at which time the treatment was terminated. The neutralized product containing 64.6 weight percent ammonium alkenyl sulfonate and 2.8 weight percent sultone was a crystal clear liquid that did not require filtration.

The term "activity" as used herein refers to the percent of polar material present in the crude sulfonation reaction and neutralized products by silica gel chromotography. A two-gram sample is diluted with 20 ml. hexane and deposited at room temperature on a 40 gram silica gel column having a 0.75 inch diameter. The unreacted polymer is eluted from the column with 250 ml. of hexane and weight obtained after evaporation of hexane. Sample weight minus weight of polymer yields total activity in sample. Sultone content is obtained by elution with 250 ml. of chloroform. Sulfonate content is total activity minus sultone.

Effective sulfonation of propene and butene polymers is obtained when the molar ratio of sulfur trioxide to polymer is in the range of 1.7 to 2.1, preferably 1.90 to 1.95. When the ratio is less than 1.7 there is inefficient sulfonation and when above 2.1 there is excessive sludge or by-product formation and loss of product. The sulfonation temperature should be in the range of 120° to 150°F. It is essential that excess sulfur trioxide be present in contact with the polymer film during its residence in the reactor so as to maximize the sulfonation reaction.

The oil-soluble sulfonates obtained by this invention are particularly useful as anti-rust agents in lubricating oils, as emulsifiers for soluble oil compositions, and as surfactants in aqueous secondary and tertiary-oil recovery operations of petroleum from underground reservoirs.

We claim:

1. The process for preparing oil-soluble ammonium alkenyl sulfonates wherein the alkenyl moiety is a propene or butene polymer having a number average molecular weight of about 250 to about 500 comprising (a) continuously treating a falling-film reactor a liquid propene or butene polymer having a number average molecular weight of about 250 to about 500 with about 1.7 to about 2.1 moles of sulfur trixoide per mol of said polymer by cocurrently passing a liquid film of said polymer and a gaseous stream of sulfur trioxide diluted with an inert gas thru said reactor while maintaining an excess of sulfur trioxide in contact with said film during passage of said liquid film thru said reactor to form a crude acid mixture comprising the corresponding alkene sulfonic acids and sultones of said polymer; (b) admixing said acid mixture with about 0.25 to about 1.25 volumes of a water immiscible inert liquid hydrocarbon solvent per volume of acid mixture and about 3 to about 20 weight percent of water based on said acid mixture, holding with agitation the aqueous mixture at a temperature of about 70° to 175°F for about 0.25 to about 2 hours, thereafter separating the aqueous and hydrocarbon solvent phases and recovering the hydrocarbon solvent organic phase containing a mixture of said oil-soluble alkenyl sulfonic acids and oil-soluble polymer sultones; (c) treating at atmospheric pressure said mixture of acids and sultones in the solvent phase of step b at a temperature in the range of from about 100°F to about 170°F with anhydrous ammonia sufficient to neutralize said sulfonic acids and provide a basic mixture comprising oil-soluble ammonium alkenyl sulfonates and oil soluble polymer sultones; and (d) heating at atmospheric pressure the mixture of step c with continuous introduction of anhydrous ammonia thereto to maintain the mixture basic to a temperature of from about 290°F to about 340°F to remove water and said hydrocarbon solvent therefrom, and thereafter holding the mixture with continued introduction of anhydrous ammonia thereto to maintain the mixture basic at said pressure and temperature for a period of time sufficient to reduce the sultone content thereof and form additional ammonium alkenyl sulfonates.

2. The process of claim 1 wherein said polymer is a butene polymer.

3. The process of claim 2 wherein step b one volume of hydrocarbon solvent is used and the amount of water is about 5 to about 10%.

4. The process of claim 3 wherein the average molecular weight of said polymer is about 300 to about 400.

5. The process of claim 4 wherein the hydrocarbon solvent in step b is hexane.

* * * * *